United States Patent [19]
Rohatgi

[11] Patent Number: 5,529,778
[45] Date of Patent: Jun. 25, 1996

[54] AYURVEDIC COMPOSITION FOR THE PROPHYLAXIS AND TREATMENT OF AIDS, FLU, TB AND OTHER IMMUNO-DEFICIENCIES AND THE PROCESS FOR PREPARING THE SAME

[76] Inventor: Surendra Rohatgi, 16/78 Civil Lines, Kanpur, Ind.

[21] Appl. No.: 304,902

[22] Filed: Sep. 13, 1994

[51] Int. Cl.$^6$ .................................................. A61A 35/78
[52] U.S. Cl. ...................... 424/195.1; 514/838; 514/885; 514/888; 514/924
[58] Field of Search .................. 424/195.1; 514/838, 514/885, 888, 924

[56] References Cited

PUBLICATIONS

Paper titled "Immunomodulating Agents of Plant Origin I: Preliminary Screening", by C. K. Atal, et al., *Journal of Ethnopharmacology*, 18, (1986) 133–141, Elsevier Scientific Publishers, Ireland, Ltd.

*Primary Examiner*—John W. Rollins
*Attorney, Agent, or Firm*—Lowe, Price, LeBlanc & Becker

[57] ABSTRACT

An ayurvedic composition for prophylaxis and treatment of AIDS, flu, TB, and other immuno-deficiency conditions, and for liver diseases such as hepatitis and sclerosis, includes prescribed doses of extracts or isolates of two multi-component drugs in selected proportions. The first multi-component drug, LIVZON, consists of Phyllanthus niruri (292–310 mg.), Tinospora cordifolia (190–210 mg.), Phyllanthus emblica (90–110 mg.), Terminalia belerica (90–110 mg.), and Terminalia chebula (290–310 mg.); and the second multi-component drug, IMMINEX, consists of Holarrhena antidysenterica (40–60 mg.), Picrorhiza kurrooa (40– 60 mg.), and Swertia chirata (15–35 mg.). The beneficial composition may be administered in the form of aqueous extracts, hard gelatin capsules, or mixed with syrup. The process of making the composition requires the basic ingredients to be cleaned, washed, dried and separated from all extraneous matter, after which they are powdered and extracts obtained therefrom with distilled water. The extracted material may be concentrated, granulated and dried at low temperature before the various ingredients are mixed in their selected proportions to form the necessary pharmaceutical dosage. Hard gelatin capsules or a syrup are other optional forms for dispensing the composition to patients.

12 Claims, No Drawings

AYURVEDIC COMPOSITION FOR THE PROPHYLAXIS AND TREATMENT OF AIDS, FLU, TB AND OTHER IMMUNO-DEFICIENCIES AND THE PROCESS FOR PREPARING THE SAME

This invention relates to ayurvedic composition for the prophylaxis and treatment of AIDS, FLU, TB as also viral, bacterial and parasitical diseases and other immunodeficiency conditions and the process for preparing the same.

BACKGROUND

AIDS is the biggest challenge to medical sciences during this century. It is said to be caused by the virus HIV (Human Immuno-deficiency Virus), which kills the helper cells of the immune system. These cells which are a part of the cell mediated immune system, play a crucial role in cell mediated immunity. With the progressive loss of the helper cells in the blood, a stage is reached where the body is rendered incapable of resisting many bacterial, viral and parasitical invasions and the AIDS patient eventually dies of these opportunistic infections. Many people have lost their lives from this disease which is wide spread throughout the world.

Scientists of the world have launched a massive research programme to develop a drug for the treatment of AIDS which has been in progress for over ten years. The approach has been to interfere with the life cycle of the HIV. The only drug approved for treatment of AIDS in different stages is zidovudine (AZT). However, it has not been found to be effective in curing a patient or saving the life of an advance case of AIDS. Recently, a joint study of British and French groups on thousands of cases in U.K. and France, titled Concord has shown the ineffectiveness of the drug AZT in controlling the progression or cure of AIDS.

A new approach has been developed which is based on enhancing cell mediated and humoral immunity by selected Ayurvedic drugs of herbal origin and simultaneously stimulating the physiological functions of the body for the treatment of AIDS. With the correction of immuno-deficiency, the body's own defensive forces selectively kill all the infecting organisms and the syndrome of AIDS disappears. An additional advantage of our new approach is the absence of adverse drug reactions which usually accompany therapies developed so far in the West.

The drug used in our new approach for the treatment of AIDS consists of two multi-component drugs of ayurvedic origin called LIVZON and IMMINEX in predetermined proportions.

According to this invention ayurvedic compositions for the prophylaxis and treatment of AIDS, FLU, TB and other Immuno-deficiency conditions, liver diseases such as hepatitis and cirrhosis etc. which comprises:

(i) LIVZON consisting of:

| | |
|---|---|
| Phyllanthus niruri | 292–310 mg. |
| Tinospora cordifolia | 190–210 mg. |
| Phyllanthus emblica | 90–110 mg. |
| Terminalia belerica | 90–110 mg. |
| Terminalia chebula | 290–310 mg. | and
(ii) IMMINEX consisting of:

| | |
|---|---|
| Holarrhena antidysenterica | 40–60 mg. |
| Picrorhiza kurrooa | 40–60 mg. |
| Swertia chirata | 15–35 mg. |

The total weight of extracts of Tinospora cordifolia, Phyllanthus emblica, Terminalia belerica and Terminalia chebula in LIVZON varies between 190–210 mgs.

This invention further relates to process for preparing the said ayurvedic composition for prophylaxis and treatment of AIDS, FLU, TB and other immunodeficiencies which comprises:
pulverising:
(i) LIVZON consisting of:

| | |
|---|---|
| Phyllanthus niruri | 292–310 mg. |
| Tinospora cordifolia | 190–210 mg. |
| Phyllanthus emblica | 90–110 mg. |
| Terminalia belerica | 90–110 mg. |
| Terminalia chebula | 290–310 mg. | and
(ii) IMMINEX consisting of:

| | |
|---|---|
| Holarrhena antidysenterica | 40–60 mg. |
| Picrorhiza kurrooa | 40–60 mg. |
| Swertia chirata | 15–35 mg. | preparing extracts or isolates thereof.
mixing the said extracts or isolates and preparing in pharmaceutical dosage form.

The total weight of extracts of Tinospora cordifolia, Phyllanthus emblica, Terminalia belerica and Terminalia chebula in LIVZON varies between 190–210 mgs.

The pharmaceutical dosage is in the form of hard gelatin capsule or liquid form mixed with syrup in the following proportion:
LIVZON:Syrup::1:15
IMMINEX:Syrup::1:75

The pharmaceutical dosages in capsule form are stored in plastic or glass containers with silica gel bags sealed with aluminium foil.

DOSAGE

One capsule normally contains LIVZON consisting of Phyllanthus niruri—300 mg and extracts of Tinospora cordifolia, Phyllanthus emblica, Terminalia belerica and Terminalia chebula—200 mg and Imminex—125 mg and may be given twice daily. This dosage may vary.

The patients are tested for HIV by Elisa and the Western Blot technique to confirm the presence of HIV 1 or HIV 2. and the CD4 (helper cells) and CD8 (suppressor cell) counts and the CD4:CD8 ratio is estimated.

One dose each of the two drugs are administered twice a day after meals to confirmed cases of 'full blown AIDS' or in the 'Carrier stage'. After a period of 1 month, the CD4 count is estimated again and the treatment continued till the count rises about 1000 and above. Even after the CD4 count reaches the figure of 2000 or so, the treatment is continued till the patient becomes HIV negative.

For prophylaxis, the drugs are administered in the same schedule mentioned above to raise the CD4 count. A person having a CD4 count of about 2000 and a CD4:CD8 ratio of nearly 2, can resist casual exposure to HIV infection. The married partner of an HIV positive person can also be protected in this manner.

An HIV positive pregnant woman has to be given one dose twice daily in order to protect the foetus. Post natally if the child shows symptoms of AIDS and tested HIV positive, one dose of each drug twice daily in syrup form should be administered till the CD4 count reaches a level normal for the age of the child. The above therapy has to be continued till the mother and child are fully protected from opportunistic infectious as indicated by the CD4 count and CD4:CD8 ratio.

During the course of treatment, all conventional drugs having an immuno suppressive activity have to be excluded.

The dose schedule can be varied according to the advise of the physician.

During the course of treatment, all drugs possessing immuno-suppressive activity are contra-indicated and are excluded from the therapy.

EXAMPLE-1

The ayurvedic compositions for the treatment of AIDS and other immunodeficiencies is prepared by:

pulversing (i) LIVZON consisting of:

| | |
|---|---|
| Phyllanthus niruri | 300 mg. |
| Tinospora cordifolia | 200 mg. |
| Phyllanthus emblica | 100 mg. |
| Terminalia belerica | 100 mg. |
| Terminalia chebula | 300 mg. | and (ii) IMMINEX consisting of:

| | |
|---|---|
| Holarrhena antidysenterica | 50 mg. |
| Picrorhiza kurrooa | 50 mg. |
| Swertia chirata | 25 mg. | preparing extracts or isolates thereof mixing the said extracts or isolates in syrup or filling the said mixture in hard gelatin capsule at 15°–18° C. in pharmaceutical dosage form.

The total weight of extracts of Tinospora cordifolia, Phyllanthus emblica, Terminalia belerica and Terminalia chebula in LIVZON is 200 mg.

The above ingredients of LIVZON and IMMINEX are cleaned, washed, dried and separated of all extraneous matter and then powdered and extracted with distilled water, the said extracts are concentrated, granulated and dried at low temperatures before mixing to form one pharmaceutical dosage.

EXAMPLE-2

The ayurvedic composition for the treatment of AIDS and other immunodeficiencies comprising (i) LIVZON consisting of:

| | |
|---|---|
| Phyllanthus niruri | 300 mg. |
| Tinospora cordifolia | 200 mg. |
| Phyllanthus emblica | 100 mg. |
| Terminalia belerica | 100 mg. |
| Terminalia chebula | 300 mg. | and (ii) IMMINEX consisting of:

| | |
|---|---|
| Holarrhena antidysenterica | 50 mg. |
| Picrorhiza kurrooa | 50 mg. |
| Swertia chirata | 25 mg. | as extracts or isolates thereof.

The total weight of extracts of Tinospora cordifolia, Phyllanthus emblica, Terminalia belerica and Terminalia chebula in LIVZON is 200 mg.

The aforesaid ingredients are cleaned, washed and separated of all extraneous matter and then powdered and extracted with distilled water individually before mixing. The extracts so obtained were concentrated and then absorbed on inert plant material, granulated and dried at low temperatures. The above mixture of LIVZON and IMMINEX is filled in a hard gelatine capsule at 15° C.–18° C., the filled capsules are kept in plastic containers with silica gel bags sealed with aluminium foils for use.

EXAMPLE 3

Aqueous extracts of the above ingredients viz. Livzon and imminex are concentrated and mixed with syrup and filled in bottles in the following proportion:

LIVZON:syrup::1:15

IMMINEX:Syrup::1:75

I claim:

1. Ayurvedic composition for the prophylaxis or treatment of a condition selected from the group consisting of AIDS, flu, tuberculosis, hepatitis, cirrhosis, and immunodeficiency conditions comprising a therapeutically acceptable amount of:

(a) LIVZON consisting essentially of distilled water extracts of the following amounts of dried plant material:

| | |
|---|---|
| Phyllanthus niruri | 292–310 mg., |
| Tinospora cordifolia | 190–210 mg., |
| Phyllanthus emblica | 90–110 mg., |
| Terminalia belerica | 90–110 mg., |
| Terminalia chebula | 290–310 mg., and |

(b) IMMINEX consisting essentially of distilled water extracts of the following amounts of dried plant material:

| | |
|---|---|
| Holarrhena antidysenterica | 40–60 mg., |
| Picrorhiza kurrooa | 40–60 mg., and |
| Swertia chirata | 15–35 mg.. |

2. Ayurvedic composition as claimed in claim 1 wherein (i) LIVZON consists of:

| | |
|---|---|
| Phyllanthus niruri | 300 mg. |
| Tinospora cordifolia | 200 mg. |
| Phyllanthus emblica | 100 mg. |
| Terminalia belerica | 100 mg. |
| Terminalia chebula | 300 mg. | and (ii) IMMINEX consists of:

| | |
|---|---|
| Holarrhena antidysenterica | 50 mg. |

-continued

| | |
|---|---|
| Picrorhiza kurrooa | 50 mg. |
| Swertia chirata | 25 mg. |

3. Ayurvedic composition as claimed in claim 1 wherein the the total weight of distilled water extracts of Tinospora cordifolia, Phyllanthus emblica, Terminalia belerica and Terminalia chebula in LIVZON varies between 190–210 mgs.

4. Ayurvedic composition as claimed in claim 1 wherein the the total weight of distilled water extracts of Tinospora cordifolia, Phyllanthus emblica, Terminalia belerica and Terminalia chebula in LIVZON is 200 mgs.

5. Ayurvedic composition as claimed in claim 1 wherein the distilled water extracts of ingredients are concentrated and mixed with syrup in the following proportion:

LIVZON:Syrup::1:15

IMMINEX:Syrup::1:75.

6. A process for preparing an ayurvedic composition for the prophylaxis or treatment of a condition selected from the group consisting of AIDS, flu, tuberculosis, hepatitis, cirrhosis, and immunodeficiency conditions comprising (a) separately pulverizing the following amounts of dried plant material to make LIVZON consisting essentially of:

| | |
|---|---|
| Phyllanthus niruri | 292–310 mg., |
| Tinospora cordifolia | 190–210 mg., |
| Phyllanthus emblica | 90–110 mg., |
| Terminalia belerica | 90–110 mg., |

IMMINEX consisting essentially of

| | |
|---|---|
| Holarrhena antidysenterica | 40–60 mg., |
| Picrorhiza kurrooa | 40–60 mg., and |
| Swertia chirata | 15–35 mg.; |

(b) preparing separate distilled water extracts of said separately pulverized dried plant material in step (a);

(c) mixing said distilled water extracts of step (b) to form a mixture; and (d) preparing a pharmaceutical formulation comprising the mixture of step (c).

7. Process as claimed in claim 6 wherein (i) LIVZON consists of:

| | |
|---|---|
| Phyllanthus niruri | 300 mg. |
| Tinospora cordifolia | 200 mg. |
| Phyllanthus emblica | 100 mg. |
| Terminalia belerica | 100 mg. |
| Terminalia chebula | 300 mg. | and (ii) IMMINEX consists of:

| | |
|---|---|
| Holarrhena antidysenterica | 50 mg. |
| Picrorhiza kurrooa | 50 mg. |
| Swertia chirata | 25 mg. |

8. Process as claimed in claim 6 wherein the the total weight of extracts of Tinospora cordifolia, Phyllanthus emblica, Terminalia belerica and Terminalia chebula in LIVZON varies between 190–210 mgs.

9. Process as claimed in claim 6 wherein the total weight of extracts of Tinospora cordifolia, Phyllanthus emblica, Terminalia belerica and Terminalia chebula in LIVZON is 200 mgs.

10. Process as claimed in claim 6 wherein the pharmaceutical dosage is in the form of a capsule and are preserved in a plastic or glass container with silica gel bags sealed with aluminium foil.

11. Process as claimed in claim 6 wherein the pharmaceutical dosage is in the form of a liquid mixed with syrup in the following proportion:

LIVZON:Syrup::1:15

IMMINEX:Syrup::1:75.

12. A process for preparing an ayurvedic composition according to claim 6, wherein said process further comprises concentrating and absorbing distilled water extracts of said mixture of step (c) on inert plant material, and granulating and drying said mixture at low temperature.

* * * * *

UNITED STATES PATENT AND TRADEMARK OFFICE
CERTIFICATE OF CORRECTION

PATENT NO. : 5,529,778
DATED : June 25, 1996
INVENTOR(S) : Surendra Rohatgi

It is certified that error appears in the above-indentified patent and that said Letters Patent is hereby corrected as shown below:

In the Abstract, line 3, change "sclerosis" to --cirrhosis--.

Column 1, line 31, change "advance" to --advanced--.

Column 2, line 60, change "2000" to --1000--;

Column 2, line 64, change "2000" to --1000--.

Column 4, line 24, change "imminex" to --Imminex--.

Signed and Sealed this

Third Day of December, 1996

*Attest:*

BRUCE LEHMAN

*Attesting Officer*    Commissioner of Patents and Trademarks